United States Patent [19]
Zisapel et al.

[11] Patent Number: 4,880,826

[45] Date of Patent: Nov. 14, 1989

[54] MELATONIN ANTAGONIST

[76] Inventors: Nava Zisapel, 23 Kissufim St.; Moshe Laudon, 14 Anderson St., both of Tel Aviv, Israel

[21] Appl. No.: 66,351

[22] Filed: Jun. 25, 1987

[30] Foreign Application Priority Data

Jun. 27, 1986 [IL] Israel ......................................... 79264

[51] Int. Cl.$^4$ ............................................ A61K 31/405
[52] U.S. Cl. .................................................... 514/415
[58] Field of Search ......................................... 514/415

[56] References Cited

PUBLICATIONS

Chem. Abstr., 108-32414c (1988).

Biochemistry, 13(18), pp. 3816–3827 (1974).

Primary Examiner—Stanley J. Friedman
Attorney, Agent, or Firm—Browdy and Neimark

[57] ABSTRACT

The invention relates to novel derivatives of melatonin, to the production of such new derivatives, to labelled forms, and especially radioactively tagged forms of such compounds, to assays for melatonin receptor function based on such radioactively tagged compounds and to pharmaceutical compositions which contain such novel non-labelled compounds.

The novel compounds are potent antagonists of melatonin which are of value in human medicine and also in animal husbandry.

5 Claims, No Drawings

MELATONIN ANTAGONIST

FIELD OF THE INVENTION

The invention relates to certain novel derivatives of melatonin (5-methoxy-N-acetyl-tryptamine), to the production of these to labelled forms of these, and to pharmaceutical compositions containing as active ingredient such a derivative.

The novel derivatives are potent antagonists of melatonin and can be used for control of reproduction in vertebrate and for medical purposes. The radioactive labelled derivatives are valuable probes for use in biochemical and medical research and can be used as probes for the study of melatonin receptors.

BACKGROUND OF THE INVENTION

The biochemical role of melatonin has been described already in Chem Eng News, May 1, 1967, p. 40.

Melatonin is one of the principal hormones secreted by the pineal gland in all vertebrates. This gland expresses an overt rhythm of melatonin production which results in the nocturnal synthesis and secretion of melatonin into the blood. The melatonin rhythm provides a signal reflecting the changing environmental lighting cycle in the organism. A large body of evidence indicates that melatonin is involved in the coordination of timed physiological processes. This is evident in seasonal breeders such as hamsters and sheep; the photoperiodic regulation of reproduction is manifested as a potent influence of melatonin on gonadal activity. Tomarkin et al, Science 227, 714 (1985). It has been shown (Zisapel et al, Res. Comm. 104 (1982) and Brain Research 246 161 (1983) that melatonin inhibits the stimulated release of dopamine from rat hypothalamus.

This provides means for the in vitro testing of putative melatonin antagonists.

SUMMARY OF THE INVENTION

There are provided novel antagonists to melatonin. There are provided radioactively labelled probes for research into the activity of and as affinity label for the identification and isolation of melatonin receptors. There are further provided pharmaceutical compositions containing such melatonin antagonists as active ingredient. Such compositions are of use, for example, in animal husbandry in the breeding of fish, reptiles, cattle and birds where they imitate in the organism the state of long photoperiods acting upon the reproductory system. They are of value in human medicine for the treatment of certain mental disorders and of endocrine disturbances. They are of value in the treatment of jet-lag, of maniac depressive states, cluster headaches, sterility, and hypertension of the blind, of disturbances occurring in shift-workers, etc and in related phenomena which result from dysfunctions of the time-keeping system (biological clock) of the organism.

The radioactively labelled derivatives may be used in order to study melatonin receptors, and in isolating these; they can be used in the study of mechanistic implications of melatonin action in timed physiological processes. Other and further features of the invention will become apparent hereinafter.

The novel compounds are derivatives of 5-methoxytryptamine and are of the folowing formula:

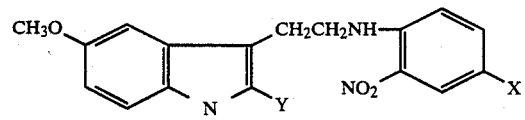

Wherein
X is —$NO_2$, —$N_3$,
Y is —H, I,
as well as radioactive labelled compounds of this type, the labelling being advantageously $^3$H-labelled and the $^{125}$I-labelled derivatives of the dinitrophenyl derivative.

The reaction of the invention comprises reacting fluorodinitrobenzene or other corresponding compounds with a primary amine, such as 5-methoxytryptamine or a functional derivative thereof.

The iodo-derivative is prepared by reacting the dinitroderivative with KI in the presence of Iodo-Gen. The azido derivative is prepared by reacting 5-methoxytryptamine with 4-fluoro-2-nitro azido benzene.

The compounds of the invention are effective for use in veterinary medicine and in husbandry, as well as in human medicine.

The compounds can be administered orally and as such can be added to food or drinking water when used in animal husbandry. Amongst various effects observed, there can be mentioned, by way of example:

(1) Long-term administration of melatonin (via the drinking water or via intraperitoneal injection) to prepubertal male rats results in retardation of testicular accessory sex organ development. Oral administration of ML-23 in the presence of melatonin entirely abolished melatonin's suppressive effects on prostate and seminal vesicle growth and on serum testosterone levels.

(2) Melatonin administration to adult female rats in the afternoon of proestrus blocks the phasic secretion of luteinizing hormone and ovulation. Administration of ML-23 to female rats via the drinking water prevented the effect of melatonin and normal ovulation occurred.

(3) Female rats kept under constant illumination become acyclical and exhibit persistent estrus characteristics. Daily melatonin injections reestablish ovarian cyclicity in these rats but not in rats treated orally with ML-23.

(4) Long-term administration of ML-23 alone to prepubertal male rats, enhanced testosterone levels in the blood of the animals.

The toxicity of the novel compounds was evaluated and it was found that they were found to be essentially non-toxic to mammals. Furthermore, body, testicular and ovarian weight of rats treated with the dinitro-compound for 4 weeks at a dosage of 800 μg/day was unchanged.

The novel active compounds are able to cross the blood brain barrier. Both derivatives reach the brain in intact form, as indicated by TLC of the labelled compounds extracted from the brain of rats which had been injected the $^3$H or the $^{125}$I labelled analogs of the drugs 30 to 60 minutes prior to sacrifice.

The synthesis is a simple one, and the starting materials are inexpensive. Yields are high and pure products are easily obtained.

The following examples illustrate the preparation of derivatives according to the present invention:

EXAMPLE 1

N-2,4-dinitrophenyl-5-methoxy-tryptamine (ML-23)

1 Mole of 5-methoxytryptamine was dissolved in 10 liters of water and the pH was adjusted to pH 8.3 with 2.5 moles of sodium bicarbonate ($NaHCO_3$), A 1.5% solution of fluoro-2,4-dinitrobenzene in 20 liters ethanol was added and the mixture was stirred during 2 hours at room temperature. The desired product precipitates out, it is washed and dried. The product is obtained in 90% yield, and TLC (chloroform, silica-gel plates, reveals one yellow spot ($r_f=0.6$) which is well resolved from the starting materials under the same conditions.

EXAMPLE 2

Production of N-2,4-Dinitrophenyl-5-methoxy-2-iodotryptamine.

The product of the preceding example was iodinated by reaction with potassium iodide iodo-Gen. The main reaction product, 2-iodo-ML-23 was separated from unsubstituted material and purified by TLC (chloroform on silica gel plates) as in the procedure described by Vakkuri et al (1984) for the iodination of melatonin. (rf of MLI-23=0.5, 60% Yield). The radioactive analogs of ML-23 and MLI-23 were prepared similarly, using 3H-fluorodinitrobenzene and carrier-free Na125I (both from Amersham).

Azido-ML-23 was prepared from 5-methoxytryptamine (0.15 mole) by reaction with 4-fluoro 2-nitro azido benzene (0.3 mole) in 1 liter of 0.23M sodium carbonate. The mixture was stirred overnight in the dark under nitrogen atmosphere at 370. The major product (rf=0.5) was separated from other products and from unreacted materials by TLC (chloroform-methanol 1:1 on silica-gel plates), iodinated with Na 125I in the presence of iodogen and separated by thin layer chromatography (rf=0.8) in chloroform on silica-gel plates.

EXAMPLE 3

Melatonin receptor assay using 2-$^{125}$I-iodo-ML-23 ($^{125}$I-MLI-23).

Tissue sections or isolated cells were suspended in 10 ml/g ice-cold 0.32M sucrose, homogenized in a teflon-glass homogenizer. The homogenate was centrifuged (10000 g-min) the pellet was discarded and the supernatant centrifuged (68000 g-min). The crude membrane pellet was suspended in 2 vol of 50 mM Tris-HCL buffer, pH 7.4 containing 4 mM $CaCl_2$. 2-$^{125}$I-iodo-ML-23 was prepared by iodination of ML-23 with Na$^{125}$I (Amersham) (20 CI/mmol) in the presence of Iodo-Gen. The principal iodination product, 2-$^{125}$ I-iodo-ML 23 ($^{125}$I-MLI-23) was separated from unsubstituted ML-23 as described in Example 2. Aliquots of the membrane preparations (200 μg protein/20 μl) were incubated with 40 μl Trisbuffer containing 20–100 nM $^{125}$I-MLI-23 for 30 min. at 37° C. on a shaking water bath, in the absence or presence of unlabelled melatonin (50 μM). Membranes were then collected by vacuum filtration using GF/C glass fiber filters and washed with 3×4 ml buffer at 4° C. The filters containing bound $^{125}$I-ML-23 were assayed for radioactivity using a Packard gamma counter. Specific binding was defined as that displaced by 50 μM of non-radioactive melatonin and ranged from 50 to 60% of the total binding at 50 nM $^{125}$I-MLI-23.

The equilibrium binding data could be fitted by non-linear regression to a single site model according to the following equation: $B = Bmax/(1+Kd/L)$ where B and Bmax are the specific binding at different $^{125}$I-MLI-23 concentrations (L) and at saturation, respectively, and Kd is the binding dissociation constant.

The distribution of melatonin binding sites in six discrete brain regions of female rats at the estrous stage and the effects of ovariectomy and subsequent 17p-estradiol treatment on these binding sites were studied using such procedure. Specific binding of $^{125}$I-MLI-23 was found in the hypothalamus, medulla-pons, hippocampus, cerebellum, striatum and parietal cortex of the female rats. Ovariectomy produced a large estradiol-reversible decrease in $^{125}$I-MLI-23 binding in the medulla-pons and hypothalamus. In contrast, $^{125}$I-MLI-23 binding sites in the other brain regions, were generally unaffected by ovariectomy or estradiol. The estradiol regulated changes in melatonin binding in the hypothalamus and medulla pons may reflect the role of a specific estradiol-melatonin interaction in coordination of the neuroendocrine reproductive axis.

We claim:

1. A pharmaceutical or veterinary composition including a physiologically acceptable carrier and containing as active ingredient a physiologically effective dosage of 5-methoxytryptamine of the formula:

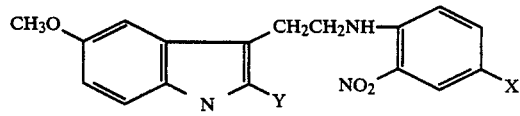

wherein

X is $-NO_2$ or $-N_3$, and

Y is $-H$ or $-I$.

2. A composition according to claim 1 wherein said compound is N-2,4-dinitrophenyl-5-methoxy tryptamine.

3. A composition according to claim 1 wherein said compound is N-2,4-nitrophenyl-5-methoxy-2-iodo tryptamine.

4. A pharmaceutical or veterinary composition according to claim 1, where the daily dosage is in the order of 0.2 mg/kg/day to about 2 mg/kg/day.

5. A pharmaceutical or veterinary composition according to claim 1, in a single dosage unit form comprising 0.2 mg to about 2 mg of said active ingredient.

* * * * *